United States Patent
Lee (10) Patent No.: US 7,065,524 B1
(45) Date of Patent: Jun. 20, 2006

(54) IDENTIFICATION AND CORRECTION OF CONFOUNDERS IN A STATISTICAL ANALYSIS

(75) Inventor: Edmund G. Lee, Palo Alto, CA (US)

(73) Assignee: Pharsight Corporation, Mountain View, CA (US)

( * ) Notice: Subject to any disclaimer, the term of this patent is extended or adjusted under 35 U.S.C. 154(b) by 1173 days.

(21) Appl. No.: 09/823,645

(22) Filed: Mar. 30, 2001

(51) Int. Cl.
G06F 17/30 (2006.01)

(52) U.S. Cl. ............................................. 707/6; 706/45
(58) Field of Classification Search .................... 707/6; 706/45
See application file for complete search history.

(56) References Cited

U.S. PATENT DOCUMENTS

| | | | |
|---|---|---|---|
| 5,060,279 A * | 10/1991 | Crawford et al. .............. | 706/20 |
| 5,491,629 A * | 2/1996 | Fox et al. ...................... | 702/3 |
| 5,606,499 A * | 2/1997 | Ostrovsky ...................... | 702/1 |
| 5,918,232 A * | 6/1999 | Pouschine et al. ...... | 707/103 R |
| 6,021,403 A * | 2/2000 | Horvitz et al. ................ | 706/45 |
| 6,026,359 A * | 2/2000 | Yamaguchi et al. ...... | 704/256.4 |
| 6,128,555 A * | 10/2000 | Hanson et al. ................ | 701/13 |
| 6,243,615 B1 * | 6/2001 | Neway et al. .............. | 700/108 |
| 6,393,387 B1 * | 5/2002 | Adriaans et al. .............. | 703/27 |
| 6,466,929 B1 * | 10/2002 | Brown et al. ................. | 706/48 |
| 6,618,721 B1 * | 9/2003 | Lee .............................. | 707/3 |
| 6,836,777 B1 * | 12/2004 | Holle ......................... | 707/101 |
| 6,850,252 B1 * | 2/2005 | Hoffberg .................... | 715/716 |

* cited by examiner

*Primary Examiner*—Wayne Amsbury
(74) *Attorney, Agent, or Firm*—Townsend and Townsend and Crew LLP (57) ABSTRACT

Systems and methods are disclosed for identifying and/or compensating for relationships between influencers and outcomes. First, a metadata model of information that characterizes relationships between influencers and outcomes is built. A query is accepted from a user, and an outcome of interest is determined based on the query. The model is subsequently relied on to flag influencers that might have an impact on an outcome of interest. The impact of these influencers on the outcome of interest is then analyzed with respect to specific conditions. When the impact is sufficiently large, the user is notified or an adjustment is made to the user's query.

33 Claims, 5 Drawing Sheets

IDENTIFICATION AND CORRECTION OF CONFOUNDERS IN A STATISTICAL ANALYSIS

BACKGROUND OF THE INVENTION

1. Field of the Invention

The present invention relates to the field of data analysis, and more specifically to identifying and/or compensating for influencers that can have an impact on a statistical outcome.

2. Background

Databases are often created as a by-product of normal operations such as health care, retail sales, and loan processing, and it is often possible to extract highly useful information by properly analyzing these databases. For example, medical researchers may obtain valuable insights into disease progression, adverse side effects of medications, or typical patient characteristics from hospital databases; buyers can identify important purchasing patterns from inventory or point-of-sale data; and bank analysts can develop fair and accurate criteria for screening loan applicants by examining the payment histories of previous borrowers.

Conventional techniques for analyzing such databases, however, are susceptible to errors that may be introduced by "confounders." Confounders are factors whose significance has been overlooked by the data analyst, but nevertheless influence the outcome of interest. An excellent example of a confounder's impact on an outcome can be found in the following data, taken from "The Effectiveness of Adjustment by Subclassification in Removing Bias in Observational Studies for Causal Effects" by W. G. Cochran, Biometrics, v. 24, pp. 295–313 (1968).

| Smoking status | Non-smoker | Cigarette smoker |
|---|---|---|
| Mortality rates per 1000 person-years | 20.2 | 20.5 |

Taking this data at face value could lead one to the incorrect conclusion that cigarette smoking is not harmful. A more in-depth analysis reveals, however, that the above results were confounded by age—it turns out that the nonsmokers represented in the database were significantly older than the cigarette smokers, with average ages of 54.9 years and 50.5 years, respectively. When the above mortality rates are adjusted for age, the results are as follows:

| Smoking status | Non-smoker | Cigarette smoker |
|---|---|---|
| Age-adjusted mortality rates per 1000 person-years | 20.2 | 29.5 |

Analysts with an in-depth understanding of a particular subject matter may be able to recognize the impact of a confounder, and eventually track down the source of error. But analysts who do not recognize the presence of a confounder may reach an incorrect conclusion.

One prior art approach for avoiding the effects of confounders is to carefully design an experiment or scientific trial using a control group. A particular factor (e.g., receiving a particular drug) is then randomly varied among the participants, and the results are observed. This approach is commonly used in medical and scientific research to verify a hypothesis. Unfortunately, this approach is very expensive to implement, because it requires performing new experiments and data analysis to test each and every hypothesis, or risking that a flawed hypothesis will be accepted and perhaps acted on.

Another prior art approach for avoiding the effects of confounders is by using preexisting data (e.g., from an existing database), and obtaining the participation of an expert in the relevant domain (e.g., a medical doctor) and a statistician to compensate for confounders for each hypothesis proposed by a data analyst. This approach can provide high quality results, but makes inefficient use of the domain expert's time and the statistician's time, who may be asked similar questions by multiple data analysts. And due to the heavy involvement of the domain expert and statistician, this prior art approach is also expensive to implement.

The inventors have recognized the need to improve the existing situation, and to enable researchers to form and verify their hypotheses more easily, without relying so heavily on freshly obtained experimental data to verify each hypothesis, and without relying on close cooperation with domain experts and statisticians.

SUMMARY OF THE INVENTION

One aspect of the invention relates to a method of identifying relationships between influencers and outcomes under a particular set of conditions. In this method, a model of information that characterizes relationships under many different conditions between influencers and outcomes is built. A query that specifies a set of conditions is inputted, and a relationship between the set of conditions specified in the query and a particular outcome that is represented in the model is determined. Based on the model, at least one potential influencer of the particular outcome is identified.

Another aspect of the invention relates to a method of identifying relationships between influencers and outcomes under a particular set of conditions. In this method, a model of information that characterizes relationships under many different conditions between influencers and outcomes is built. A query that specifies a set of conditions is inputted, and a relationship between the set of conditions specified in the query and a particular influencer that is represented in the model is determined. A relationship between the query and a particular outcome that is represented in the model is also determined. Based on the model, at least one potential influencer of the particular outcome is identified. This potential influencer is unaccounted for by the query.

Another aspect of the invention relates to a method of identifying relationships between influencers and outcomes under a particular set of conditions. In this method, a model of information that characterizes relationships under many different conditions between a plurality of nodes is built. In this model, at least some of the nodes represent influencers and at least some of the nodes represent outcomes. A query that relates to at least one of the nodes is inputted, and a relationship is determined between the query and the nodes of the model. Based on the model, a potential influencer of an outcome associated with the query is identified.

DETAILED DESCRIPTION OF THE PREFERRED EMBODIMENTS

Figure 1:
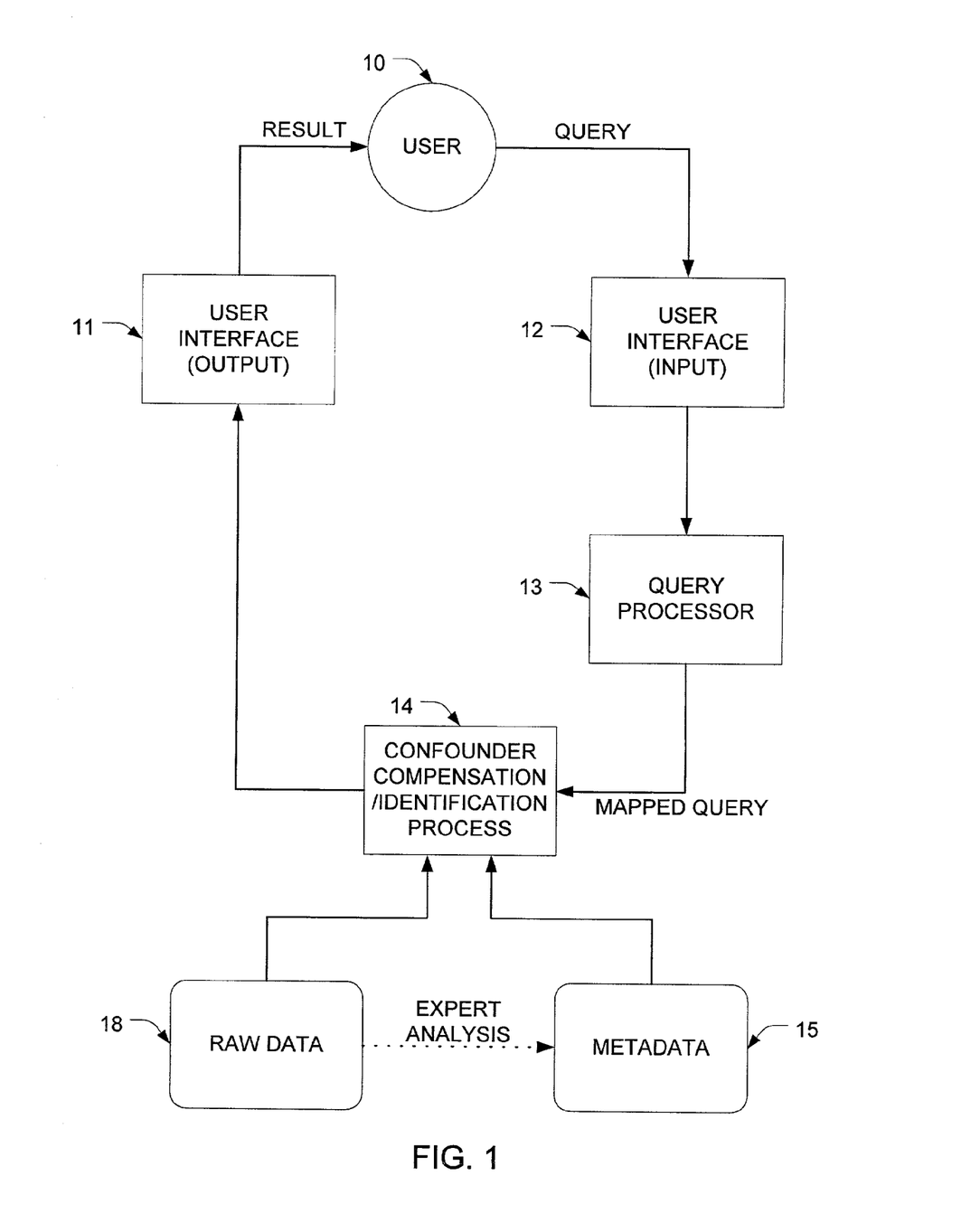
FIG. 1 is a functional block diagram of a preferred embodiment of the present invention.

FIG. 1 is a functional block diagram of a preferred embodiment of the present invention. The illustrated functions are preferably implemented using conventional computer hardware and peripherals. A user 10 provides inputs to the system via input interface 12, and receives outputs from the system via output interface 11. A query processor 13 accepts the user's input from the input interface 12. The input interface 12 may be implemented using any of a variety of conventional techniques, such as graphical, command-line, or natural language interfaces. Inputted queries are submitted to the query processor 13, which parses each query and submits the parsed query to the confounder compensation/identification process 14 (hereinafter "CCIP"). Parsed queries may be represented in a variety of ways, such as SQL select statements or natural language expressions. The CCIP 14 accepts the parsed query, implements a process to determine a result, and sends the result to the user 10 via the output interface 11. The result may be presented using any suitable user interface technique, such as text, tabular or graphical displays, or combinations thereof.

Examples of the processes implemented in the CCIP 14 are described below. Preferably, the CCIP 14 has access to metadata 15 and to a raw data database 18. The metadata 15 and the raw data database 18 may be, for example, relational database systems, computer file systems, or other systems that are capable of maintaining the required data.

Compensation for confounders relies heavily on metadata 15. The metadata 15 may be generated by human experts in a particular field of study (aided by statisticians when necessary), by a computerized process that recognizes relationships within a body of raw data (using, for example, statistical techniques or artificial intelligence methods), or by a combination of human and computerized processes.

Preferably, the metadata 15 specifies whether a relationship exists between a plurality of influencers and outcomes. Optionally, the metadata 15 may also describe a characteristic of that relationship. The metadata 15 is preferably established so as to encode both expert domain information and statistical opinion information. Because this information is encoded into the metadata 15, it can be subsequently extracted from the metadata 15 by an automated process (including, e.g., the processes described below). The metadata 15 can serve as a repository for the experts' knowledge concerning the various influencers and outcomes. Consulting this repository enables data analysts to obtain the benefit of this knowledge without actually consulting a live expert.

Once the metadata 15 has been established, it is stored in a suitable media (e.g., RAM, hard disks, etc.) for access by the processes described below. The mechanics of storing and accessing the metadata 15 may be implemented in any conventional manner, using any of a variety of conventional database programs running on conventional computer hardware (not shown).

Figure 2A:
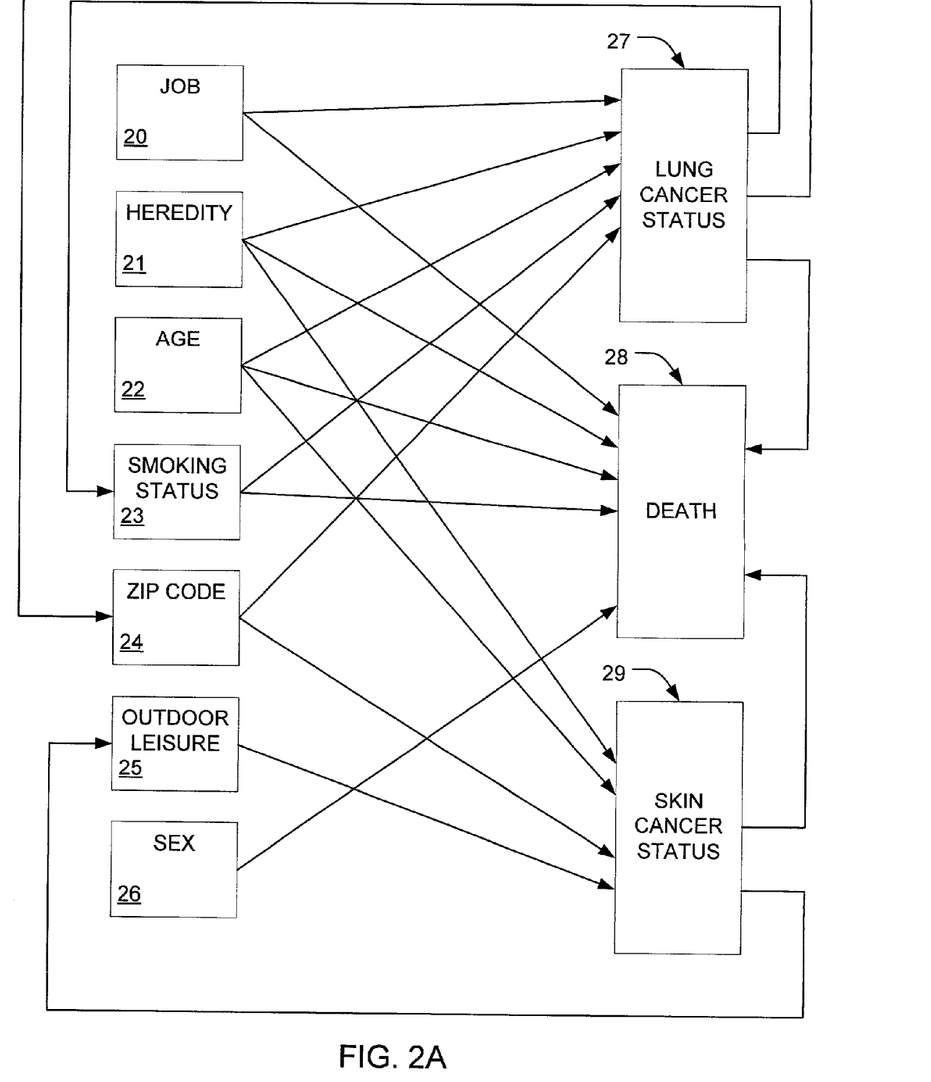
FIG. 2A is a pictorial representation of a first metadata model depicting relationships between influencers and outcomes.

FIG. 2A is an example (in the context of the health field) of a directed graph of relationships that may be used as the metadata 15 in the processes described herein. In the illustrated directed graph, nodes represent influencers and outcomes, and directed edges represent relationships. Although other representations are feasible, a directed graph representation is convenient for visual presentation during the development of the metadata model by domain and statistical experts because it assists visualization of the relationships that exist between the various influencers and outcomes. It can also be easily translated into a format that can be accessed by the CCIP 14 (shown in FIG. 1).

In the example shown in FIG. 2A, nodes 20–26 appear on the left side of the figure, and nodes 27–29 appears on the right side of the page. When a causal relationship exists between two nodes, a directed edge is shown as an arrow from the influencer to the outcome. When no such relationship exists between two nodes, no directed edge is shown between those nodes. In the illustrated example, nodes 20–26 are all influencers of one or more of the nodes 27–29 (for example, smoking status 23 increases the probability of lung cancer 27). Nodes 23, 24, and 25 are also outcomes, because they are affected by the state of the nodes 27 and 29 (e.g., lung cancer status 27 may cause a person to quit smoking, and move to a zip code with cleaner air). Nodes 27 and 29 are both influencers and outcomes, and node 28 is an outcome only. Of course, in the context of health, the relationships illustrated in FIG. 2A represent only a small subset selected from the potential universe of entries that could impact the various illustrated outcomes. Preferably, all factors known to have a significant impact on each of the outcomes should be included in the metadata 15.

Figure 2B:
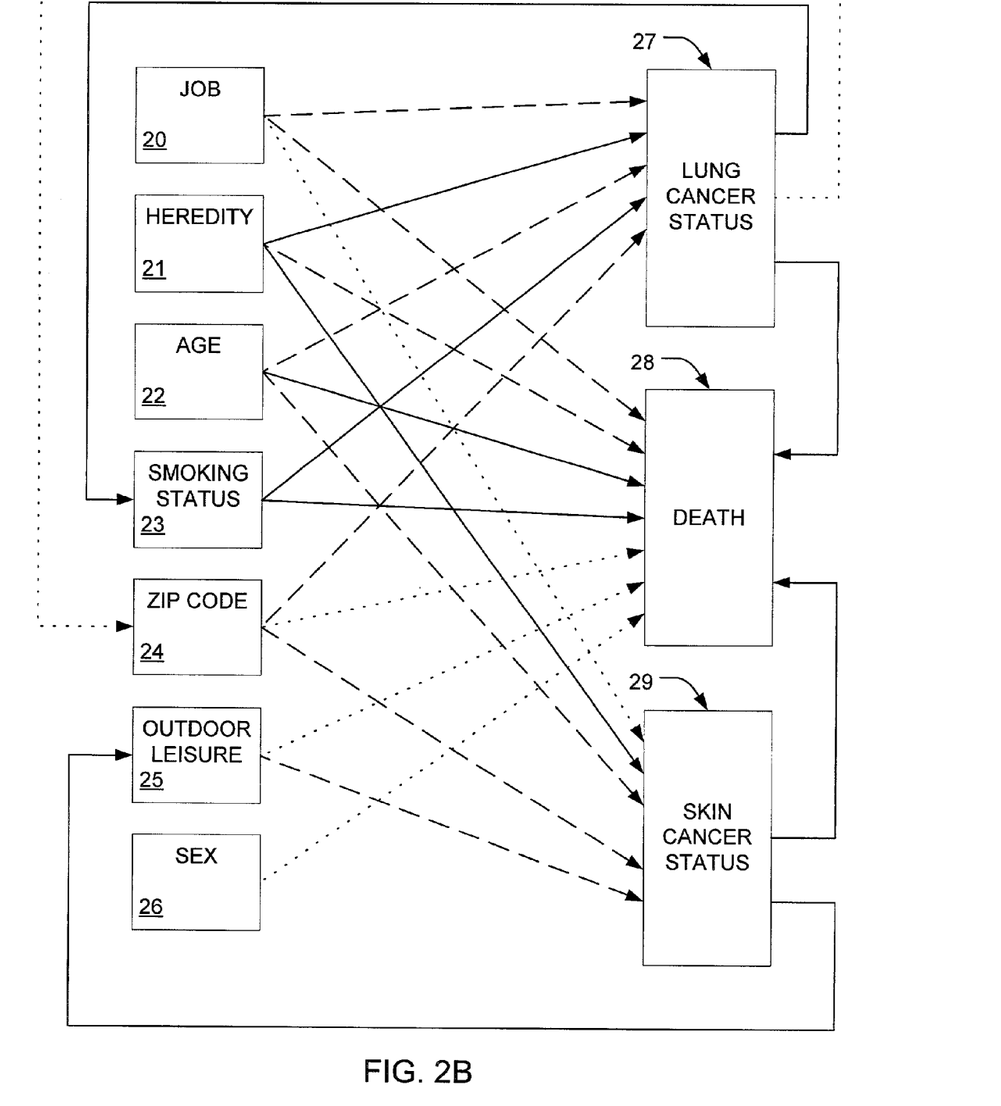
FIG. 2B is a pictorial representation of a second metadata model depicting relationships between influencers and outcomes.

FIG. 2B is another example of a directed graph of relationships that that may be used as the metadata 15 in the processes described herein. FIG. 2B is similar to FIG. 2A, except that additional information about the strength of each relationship is included. In FIG. 2B, strong relationships are indicated by solid lines, medium relationships by dashed lines, and weak relationships by dotted lines.

Figure 3:
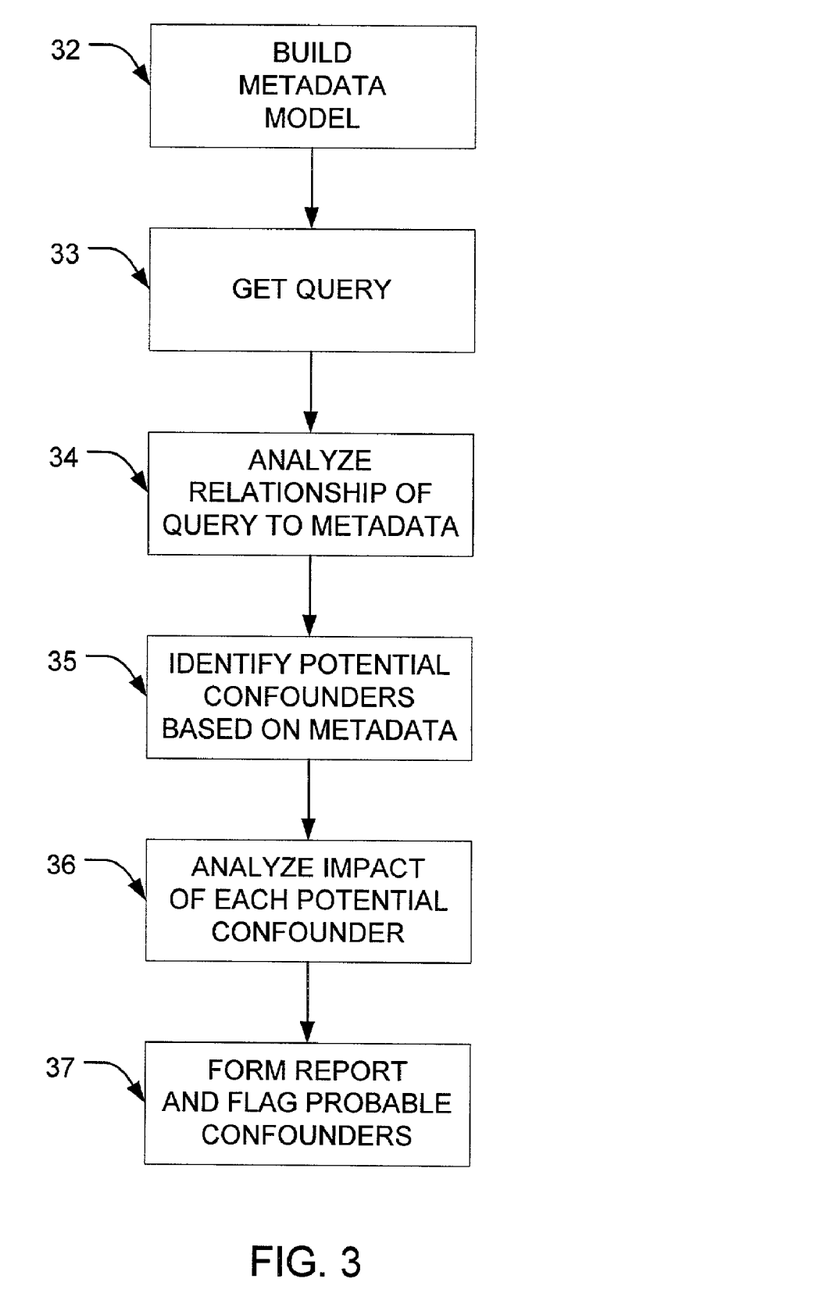
FIG. 3 is flowchart of a method for identifying potential confounders and reporting those confounders to a user.

FIG. 3 illustrates a "diagnostic" mode of operation, where the metadata is used to identify potential confounders and to report those confounders to the user. In step 32, the metadata model is formed to define a set of relationships between the influencers and the outcomes. Examples of forming the metadata model are described above in connection with FIGS. 2A and 2B. This step is preferably implemented before the remaining steps (e.g., days or even months in advance).

In step 33, the system accepts a query from the user (via the input interface 12, shown in FIG. 1), and the influencers, outcomes, and relationships contained in that query are captured by the system. Queries from the user may take any number of forms. Some forms will identify only an influencer (e.g., "what are the bad effects of smoking?") or only an outcome (e.g., "tell me the factors that influence lung cancer status"). Other queries may include both influencers and outcomes (e.g., "is there a relationship between rate of death and a subject's zip code?"). Still other queries may include the nature of the relationship between the influencers and the outcomes in an imprecise manner, either implicitly (e.g., "show me rates of death for smokers and non-smokers") or explicitly (e.g., "does smoking increase the risk of lung cancer?"). Other queries may include the nature of the relationship between the influencers and the outcomes in a more precise manner (e.g., does smoking two packs of low-tar cigarettes a day increase the risk of lung cancer by a factor of four?"). In some cases, a query may involve more than one influencer or outcome (e.g., "what is the death rate of diabetics that also have skin cancer, as compared to the general population?").

Queries may be accepted in step 33 in any desired format, including, for example, statements, questions, and lists of terms, as long as the query processor 13 (shown in FIG. 1) is programmed to handle the desired input format. Any suitable input interface 12 (shown in FIG. 1) may be used for inputting the query. One example is to provide a set of text-input fields on a computer-generated display, and to display an appropriate message (e.g., "to investigate the relationship between an influencer and an outcome, type one or more influencers in field A, an outcome in field B, then click "go"). Another example of a suitable user interface would be to select an influencer, an outcome, and a relationship from drop-down menus that are populated based on the contents of the metadata 15. Similar arrangements can be readily envisioned for various different query types, including those described above. Queries may also be accepted from the user in plain English (or any other language) using natural-language recognition software. In this case, a user would be able to type (or speak) a complete statement of their query using any conventional user interface. Alternative user interfaces can be readily envisioned.

The end result of the query accepting step is a set of influencers, outcomes, and relationships. Depending on the particular query that was inputted by the user, this set may contain only influencers, only outcomes, or both influencers and outcomes. If relationships were also inputted by the user, these relationships would also be included in the set.

In step 34, the terminology that was used in the inputted query is analyzed to determine which entries in the metadata are implicated by the query. In cases when the query uses the exact same terminology as the metadata, this step may be implemented by looking up the query terms in a table that contains all the metadata terms. When the identical terminology is not used, the query terminology must be analyzed to map the query terms onto the metadata terms before subsequent processing can occur. For example, if the metadata contains a relationship indicating links skin cancer and death, but the query used the terminology "how long do people with melanomas usually live?" The query term "melanoma" must be associated with "skin cancer" in the metadata, and the query terms "how long" and "live" must be associated with "death" in the metadata. This correspondence may be implemented, for example, using a thesaurus. More sophisticated language-recognition algorithms may also be used. In certain cases, an appropriate computation may be required to match the query terminology with the metadata. For example, if the metadata includes "age," but the query relates to date of birth, subtraction would be appropriate. Similar conversions may also be required when the raw data is accessed. The end result of this step is the set of metadata concepts that were recognized in the query, referred to hereinafter as "recognized concepts."

In step 35 the metadata is analyzed, preferably for each of the recognized concepts, to determine which things in the metadata influence the recognized concepts, and/or which things in the metadata are influenced by the recognized concepts. In the examples of FIGS. 2A and 2B, this may be accomplished by noting which nodes are linked to each of the recognized concepts by a directed edge. Any node in the metadata that has an influence on one of the recognized concepts (and has not already been accounted for in the query) is identified as a potential confounder. For example, if a query asks for the relationship between outdoor leisure and skin cancer for a particular age group, examination of the FIG. 2A metadata model would reveal that zip code and heredity are potential confounders of the "skin cancer" outcome. Optionally, when the strength of the relationships are encoded in the metadata (as shown in FIG. 2B), the user may be provided with an option to set a threshold that would exclude relationships classified as "weak" or "medium" from being identified.

In step 36, the impact of each of the identified potential confounders on the query is analyzed to determine whether, under the circumstances presented by the query, the potential confounder is likely to have an impact on the outcome. This step is preferably implemented by having the CCIP 14 access the raw data database 18 (both shown in FIG. 1) to determine whether the confounder is implicated by the subpopulation delineation called for by the query. The database may be accessed using conventional database accessing techniques such as SQL queries in conjunction with conventional statistical techniques.

The concept of subpopulation delineation can be understood in the context of the following example, where the query is "do females have a higher incidence of skin cancer than males"? In this example, age would be identified as a potential confounder for the outcome of "skin cancer" based on the metadata. Based on the query, the universe is divided into two subpopulations—males and females. If the age distribution in these two subpopulations is different, age is likely to have an impact on the outcome, and is accepted as a probable confounder. But if the age distribution in the two subpopulations is similar, then age is unlikely to have an impact on the outcome, and would not be a probable confounder (despite the fact that the metadata indicates a causal relationship may exist between smoking and death).

Note that step 36 is optional, and may be omitted. In this case, the potential confounders would be reported below in step 37 (instead of the probable confounders).

In step 37, a response to the original query is reported to the user. Preferably, this response is based on an analysis of the raw data 18 by the CCIP 14 data (both shown in FIG. 1), and is responsive to the presented query. For example, for the query "how do the mortality rates for smokers and nonsmokers compare?", the reported result could be something like "the mortality for smokers and nonsmokers are as follows . . . ". In addition to the response to the original query, any probable confounders that were identified in step 36 are reported to the user (or, if step 36 was omitted, the potential confounders). For example, in cases where age impacts the mortality rate, a suitable message (e.g., "WARNING: you did not indicate an age range for the subjects, which would have a significant impact on the reported results") would be presented to the user. Both the response to the query and the reporting of confounders are preferably presented to the user via output interface 11 (shown in FIG. 1) using any user interface technique appropriate for the data being displayed (e.g., pop-up display windows paragraphs of text, tabular displays, graphic displays, etc.).

Optionally, an additional level of detail may be provided when reporting a confounder. For example, if the inputted query was "show me the mortality rates for smokers and non-smokers," and step 36 identified age as a probable confounder, the system could generate a message such as "WARNING: the results provided above do not account for age—the average age of the smokers in the examined database is 45, but the average age of non-smokers is 57." The user could subsequently use this information to refine their query.

Figure 4:
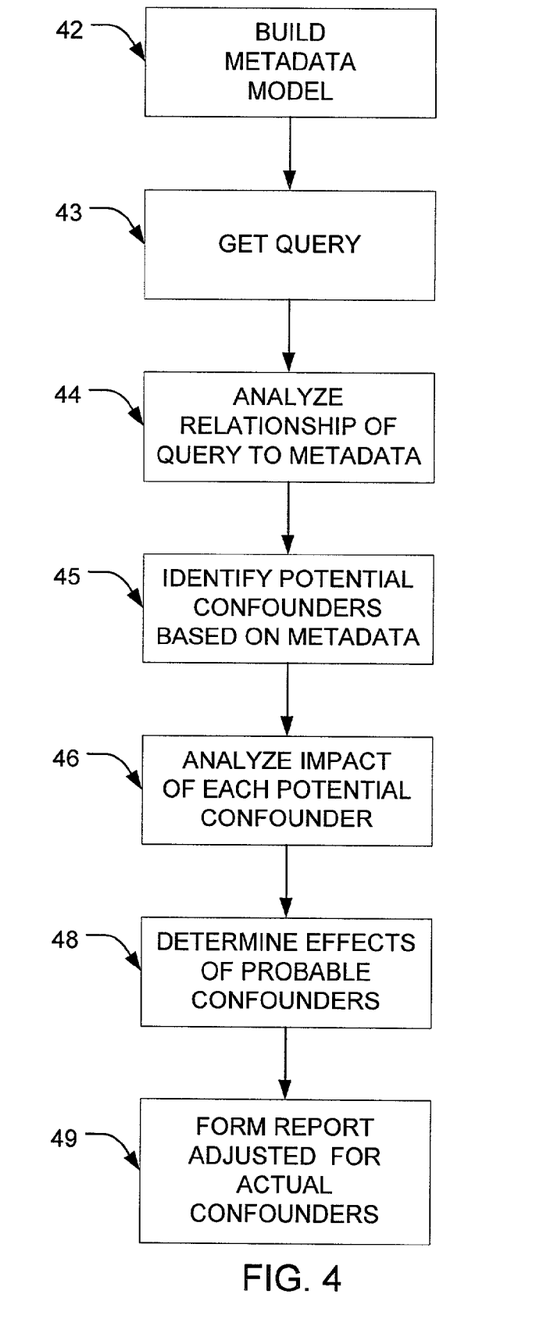
FIG. 4 is flowchart of a method for identifying potential confounders and adjusting for the impact of those confounders.

FIG. 4 illustrates a "statistical-analytic" mode of operation, where the metadata is used to actually adjust or correct a query. Steps 42–46 of this embodiment are similar to steps 32–36 of the embodiment described above in connection with FIG. 3.

After steps 42–46 have been implemented (i.e., after all the probable confounders have been identified), processing proceeds to step 48 where, the actual impact of the probable confounders on the query is computed for the particular situation in question. This step is preferably implemented by having the CCIP 14 access the raw data database 18 (both shown in FIG. 1), using conventional database accessing techniques such as SQL queries in conjunction with conventional statistical techniques. For example, if the inputted query was "show me the mortality rates for smokers and non-smokers," and age was identified as an probable confounder in step 46, the CCIP 14 could interrogate the database using appropriate SQL queries for the age group in question to determine the actual impact of heredity on skin cancer. If the impact is sufficiently large, the probable confounder "heredity" would be recognized as an actual confounder under the particular set of circumstances delineated by the query.

Statistical techniques for determining the effects of probable confounders may be chosen on the basis of many factors, including computational and statistical resources available in the query processor 13, the CCIP 14, types of entities (e.g., continuous vs. discrete), relationships between a confounder and outcome, and the ability of an end user to understand the technique and its output. For many queries, the appropriate analysis involves comparing the distribution of probable confounders in two groups, such as "smokers" vs. "non-smokers." For individual confounders, applicable techniques may include descriptive statistics, graphical summaries, or Student's t statistic comparing the means for each group. It may be necessary to consider groups of confounders, in which case multi-way analyses of variance may be appropriate. Propensity scores may also be used to analyze the relevant data, either alone or in conjunction with other statistical analysis techniques.

One example of the application of statistical techniques to the database analysis is age-normalization. For example, to determine whether smoking contributes to mortality for a particular subpopulation, the system can divide the subpopulation into a number of age groups (e.g., into five age groups), and compute the mortality rates for both the smokers and nonsmokers in each age group. The average of the five smoking numbers are then compared to the average of the five non-smoking numbers, and an age-adjusted mortality rate is determined. If the age-adjusted mortality rate differs from the non-adjusted mortality rate, this would indicate that age is an actual confounder for the particular circumstance presented by the query.

Once the actual impact of the confounder has been determined, the query is adjusted accordingly. For example, if the inputted query was "show me the mortality rates for smokers and non-smokers," and age was identified as an probable confounder in step 46, the system would first determine the impact of the confounder on the query (i.e., the impact of age), and then adjust the query to take the confounder into account. In this example, the query adjustment can be implemented by changing "mortality rate" to "age-adjusted mortality rate." The specifics of adjusting the query to compensate for the confounders will depend on the form of the query, and may be implemented, for example, using a suitable language processor.

Once the appropriate adjustment to the query has been determined, processing proceeds to step 49 where the adjusted query is presented to the user together with the results for the adjusted query (via the output interface 11 shown in FIG. 1). In the current example, one appropriate presentation would be "the AGE-ADJUSTED mortality rates for smokers and non-smokers are as follows . . . ". Preferably, any modifications that were made to the query are flagged to the user in a suitable manner (e.g., by highlighting them, using italics, or generating up a suitable explanatory message in a pop-up window).

The above-described embodiments can advantageously be used to either flag probable confounders, so that a data explorers can re-formulate their hypothesis, or to compensate for the effects of the confounders. It can also be used to reduce reliance on the expensive and time consuming process of obtaining fresh experimental data to validate each hypothesis, thereby making the data-explorer's efforts more productive. It can also help amortize the cost of domain and statistical knowledge across many data-explorers working in the same general field, because the metadata and processing steps allow reuse of the domain and statistical knowledge numerous times once it has been captured.

It should be noted that while the above-described embodiments have been explained in the context of health care, they are equally applicable in other fields, including, but not limited to, finance, retail sales, agriculture, etc. Moreover, while the present invention has been explained in the context of the preferred embodiments described above, it is to be understood that various changes may be made to those embodiments, and various equivalents may be substituted, without departing from the spirit or scope of the invention, as will be apparent to persons skilled in the relevant arts.

What is claimed is:

1. A computer implemented method of identifying a confounder, the method comprising the steps of:
  building a model of information that characterizes relationships under many different conditions between influencers and outcomes;
  storing metadata in a computer readable storage medium as a part of the model, the metadata specifying,
    whether a relationship exists between an influencer and an outcome, and
    a characteristic of that relationship, including whether the influencer represents a confounder of the outcome;
  inputting to a user interface a query that specifies a set of conditions;
  determining a relationship between the set of conditions specified in the query and a particular outcome that is represented in the model;
  identifying, based on the metadata of the model, at least one potential influencer of the particular outcome, and whether the potential influencer represents a confounder of the particular outcome; and
  if the potential influencer represents a confounder of the particular outcome, reporting the confounder to the user interface.

2. The method of claim 1, further comprising the step of analyzing whether the at least one influencer identified in the identifying step is expected to have a significant impact on the particular outcome.

3. The method of claim 2, further comprising the step of reporting, based on a result of the analyzing step, an expected impact.

4. The method of claim 1, further comprising the step of analyzing the effect of the at least one influencer identified in the identifying step on the particular outcome.

5. The method of claim 4, further comprising the step of generating a modified query based on a result of the analyzing step.

6. The method of claim 4, wherein analyzing the effect comprises at least one of comparing distributions of probable confounders in multiple groups of conditions, employing descriptive statistics, employing graphical summaries, employing Student's t statistics, considering groups of confounders utilizing multi-way variance, and employing propensity scores.

7. The method of claim 1, wherein the determining step comprises a natural language recognition process.

8. The method of claim 1, wherein, in the building step, the model is built with the metadata based on at least one of computerized data analysis and opinions of human experts in a particular field.

9. The method of claim 1, wherein the metadata is stored in the computer readable storage medium comprising one of a random access memory (RAM) and a hard disk.

10. The method of claim 1, wherein the metadata comprises a directed graph representation.

11. The method of claim 1, wherein the metadata encodes at least one of expert domain information and statistical opinion information.

12. A computer-implemented method of identifying relationships between influencers and outcomes under a particular set of conditions, the method comprising the steps of:
building a model of information that characterizes relationships under many different conditions between influencers and outcomes;
storing metadata in a computer readable storage medium as a part of the model, the metadata specifying,
whether a relationship exists between an influencer and an outcome, and
a characteristic of that relationship, including whether the influencer represents a confounder of the outcome;
inputting to a user interface a query that specifies a set of conditions;
determining a relationship between the set of conditions specified in the query and a particular influencer that is represented in the model;
determining a relationship between the set of conditions specified in the query and a particular outcome that is represented in the model;
identifying, based on the metadata of the model, at least one potential confounder of the particular outcome, wherein the potential confounder is unaccounted for by the query; and
reporting the confounder to the user interface.

13. The method of claim 12, further comprising the step of analyzing whether the at least one influencer identified in the identifying step is expected to have a significant impact on the particular outcome.

14. The method of claim 13, further comprising the step of reporting, based on a result of the analyzing step, an expected impact.

15. The method of claim 13, wherein the analyzing step comprises comparing a computed impact to a threshold.

16. The method of claim 12, further comprising the step of analyzing the impact of the at least one influencer identified in the identifying step on the particular outcome.

17. The method of claim 16, further comprising the step of generating a modified query based on a result of the analyzing step.

18. The method of claim 12, wherein the query inputted in the inputting step defines a relationship between an influencer and an outcome.

19. The method of claim 12, wherein each of the determining steps comprises a natural language recognition process.

20. The method of claim 12, wherein, in the building step, the model is built with the metadata based on at least one of computerized data analysis and opinions of human experts in a particular field.

21. A computer-implemented method of identifying relationships between influencers and outcomes under a particular set of conditions, the method comprising the steps of:
building a model of information that characterizes relationships under many different conditions between a plurality of nodes, wherein at least some of the nodes represent influencers and at least some of the nodes represent outcomes;
storing metadata in a computer readable storage medium as a part of the model, the metadata specifying,
whether a relationship exists between an influencer and an outcome, and
a characteristic of that relationship, including whether the influencer represents a confounder of the outcome,
inputting to a user interface a query that relates to at least one of the nodes;
determining a relationship between the query and the nodes of the model; and
identifying, based on the metadata of the model, a potential influencer of an outcome associated with the query, and whether the potential influencer represents a confounder of the outcome; and
if the potential influencer represents a confounder of the outcome, reporting the confounder to the user interface.

22. The method of claim 21, further comprising the step of analyzing—whether the potential influencer has a significant impact on the outcome associated with the query.

23. The method of claim 22, further comprising the step of reporting instances in which the potential influencer is expected to have a significant impact on the outcome associated with the query.

24. The method of claim 22, further comprising the step of generating a modified query in instances where the potential influencer has a significant impact on the outcome associated with the query.

25. The method of claim 22, wherein the analyzing step comprises comparing a computed impact to a threshold.

26. The method of claim 22, wherein the query inputted in the inputting step defines a relationship between an influencer and an outcome.

27. The method of claim 22, wherein the determining step comprises a natural language recognition process.

28. The method of claim 22, wherein, in the building step, the metadata of the model is built based on at least one of computerized data analysis and opinions of human experts in a particular field.

29. The method of claim 22, wherein the potential influencer identified in the identifying step is not represented in the query.

30. The method of claim 22, wherein the metadata is stored in the computer readable storage medium comprising one of a random access memory (RAM) and a hard disk.

31. The method of claim 22, wherein the metadata comprises a directed graph representation.

32. The method of claim 22, wherein the metadata encodes at least one of expert domain information and statistical opinion information.

33. The method of claim 22, wherein analyzing the impact comprises at least one of comparing distributions of probable confounders in multiple groups of conditions, employing descriptive statistics, employing graphical summaries, employing Student's t statistics, considering groups of confounders utilizing multi-way variance, and employing propensity scores.

* * * * *